United States Patent [19]

Fritsch et al.

[11] Patent Number: 4,725,536
[45] Date of Patent: Feb. 16, 1988

[54] REAGENT POLYNUCLEOTIDE COMPLEX WITH MULTIPLE TARGET BINDING REGIONS, AND KIT AND METHODS

[75] Inventors: Edward F. Fritsch, Concord; Mary Collins, Natick, both of Mass.

[73] Assignee: Genetics Institute, Inc., Cambridge, Mass.

[21] Appl. No.: 777,796

[22] Filed: Sep. 19, 1985

[51] Int. Cl.⁴ .................. C12Q 1/68; G01N 33/566
[52] U.S. Cl. ........................ 435/6; 435/810; 436/501; 935/77; 935/78; 536/26; 536/27; 536/28
[58] Field of Search ............. 435/6, 810; 436/501; 935/77, 78; 536/27, 28, 26

[56] References Cited

U.S. PATENT DOCUMENTS 4,563,417 1/1986 Albarella et al. .............. 435/7 X

FOREIGN PATENT DOCUMENTS 2559783 8/1985 France .
2139349 11/1984 United Kingdom .................. 935/77

Primary Examiner—Robert J. Warden
Assistant Examiner—Jack Spiegel
Attorney, Agent, or Firm—Alan M. Doernberg

[57] ABSTRACT

Reagent complexes containing a probe polynucleotide with at least two target binding regions. A labeled polynucleotide is bound to at least a portion of each target binding region. In one method, sample nucleic acid displaces labeled polynucleotide from one target binding region; after washing, a reagent polynucleotide displaces labeled polynucleotide from the other target binding region. In a second method, sample nucleic acid strands having two target nucleic acid sequences in proximity (e.g., sequences translocated in certain cancers) displace the labeled polynucleotide from both target binding region.

21 Claims, 14 Drawing Figures

REAGENT POLYNUCLEOTIDE COMPLEX WITH MULTIPLE TARGET BINDING REGIONS, AND KIT AND METHODS

BACKGROUND OF THE INVENTION

The present invention relates to polynucleotide reagents for the determination of target nucleotide sequences, and to diagnostic kits and methods employing such polynucleotide reagents.

A group of six inventors, including the present applicants, have described in applications U.S. Ser. No. 607,885, filed May 7, 1984, 684,305, filed Dec. 20, 1984, and 684,308, filed Dec. 20, 1984, reagent complexes and their use in diagnostic kits and methods. Such reagent complexes contain a probe polynucleotide (P) having a target binding region (TBR) substantially complementary to the target nucleotide sequence being determined, and a labeled polynucleotide (L) or signal strand (SS) as it is referred to in later applications, bound by complementary base pairing to at least some of the nucleotides of the target binding region (TBR) of the probe polynucleotide (P). In the method, a sample polynucleotide (G) displaces the signal strand from the reagent complex. Frequently, after a separation, the displaced signal strand (or labeled polynucleotide) is detected.

There is a brief discussion in each of U.S. Ser. No. 607,885, 684,305 and 684,308 of detecting two different target nucleotide sequences in a sample by employing two different reagent complexes, each with a unique label, and each with a target binding region substantially complementary to one of the two target nucleotide sequences.

Sandwich polynucleotide assays have been described, e.g., in U.S. Pat. No. 4,486,539 (1984), in which two probe polynucleotides are used, each complementary to a portion of the target nucleotide sequence. Sample polynucleotide having such a target nucleotide sequence binds to both probes, one immobilized, the other in solution and bearing a label, e.g., a radiolabel. After washing, the detectable label present on the surface is intended to be limited to those labeled probes bound via sample to the immobilized probes. Again, the two portions of the target nucleotide sequence are complementary to sequences of two separate probe polynucleotides. See also EPA No. 139,489 (May 2, 1985).

BRIEF DESCRIPTION OF THE INVENTION

Figure 1A:
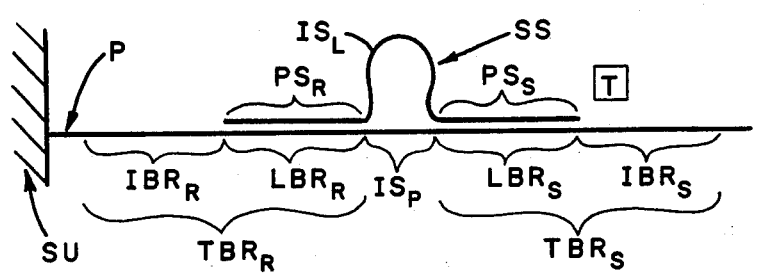
FIG. 1, in four parts, is a schematic view of a first embodiment of the present invention, in which a reagent complex (FIG. 1A) is contacted with a sample polynucleotide G (in FIG. 1B) and then a reagent polynucleotide RP (in FIG. 1C and 1D) to displace a signal strand SS in accordance with the first method of the present invention.

The present invention provides a reagent complex for the determination of a predetermined target nucleotide sequence in the nucleic acid of a biological sample comprising:

(a) a probe polynucleotide having:

(i) a first target binding region which is capable of complementary base pair binding via hydrogen bonds of purine/pyrimidine base pairs to the target nucleotide sequence; and (ii) a second target binding region which is capable of complementary base pair binding via hydrogen bonds of purine/pyrmimdine base pairs to a selected nucleotide sequence; and (b) a labeled polynucleotide which is bound by complementary base pair binding via hydrogen bonds of purine/pyrimidine base pairs to the probe polynucleotide in at least a portion of the first target binding region and in at least a portion of the second target binding region.

The present invention further provides a diagnostic kit comprising the above reagent complex and a polynucleotide reagent containing the selected nucleotide sequence.

The present invention further provides a first method, which is a method for the determination of a predetermined target nucleotide sequence in the nucleic acid of a biological sample, comprising the steps:

(I) contacting the sample with the above reagent complex under conditions in which the target nucleotide sequence, if present, displaces the labeled polynucleotide from first target binding region;

(II) washing the reagent complex:

(III) further contacting the washed reagent complex with a polynucleotide reagent comprising the selected nucleotide sequence under conditions in which the selected nucleotide sequence displaces the labeled polynucleotide from the second target binding region; and (IV) detecting labeled polynucleotide displaced from the first and second target binding regions.

The present invention further provides a second method, which is a method for determining the presence of a target nucleotide sequence and a selected nucleotide sequence within a common polynucleotide strand of the nucleic acid of a biological sample, which comprises the steps:

(I) contacting the sample with the above reagent complex under conditions, including sufficient molar excess of reagent complex relative to anticipated levels of the target nucleotide sequence and of the selected nucleotide sequence, under which sample nucleic acids having the target nucleotide sequence and the selected nucleotide sequence, if present within a common sample polynucleotide strand, will displace substantially more labeled polynucleotide strands from the first and second target binding regions of a common probe strand than will target nucleotide sequences and selected nucleotide sequences on separate sample polynucleotide strands; and (II) detecting labeled polynucleotides displaced from the first and second target binding regions of a common probe strand.

DETAILED DESCRIPTION OF THE INVENTION

The terminology used in this disclosure is that of application Ser. No. 607,885 of Diamond, et al. (including the present inventors as co-applicants), hereby incorporated by reference.

The present invention, in its broadest form, is a reagent complex having a probe polynucleotide with at least two target binding regions and a labeled polynucleotide (or signal strand) bound by complementary base pairing to at least a portion of at least two target binding regions (TBRs). For simplicity, the description will generally refer to two such TBRs (with extension to three or more TBRs discussed below).

The methods of the present invention are each based upon the principle that the signal strand SS will be released from the probe if and only if it is displaced from both TBRs, which should require contact by nucleotide sequences complementary to both TBRs. At least one of the two complementary sequences is a target nucleotide sequence being analyzed. Unlike the methods described in U.S. Ser. No. 607,885, contact and displacement by such target nucleotide sequence (TNS) alone is insufficient, in the present invention, to cause a complete displacement of the signal strand.

For the first method of the invention, the second TBR is complementary to a polynucleotide sequence present in a polynucleotide reagent. The reagent, generally in excess, contacts the reagent complex after contact by sample. While such polynucleotide reagent will displace many, most or even all of the signal strands from the second target binding regions (or $TBR_R$), not all such signal strands will be released from the probe. Instead, only those signal strands which have been displaced from the first target binding region (TBRs) and are now displaced from the second target binding region ($TBR_R$) are released from the probe (for later detection). Separation of probe and intact reagent complexes (generally on a solid phase by this time) from totally released signal strands (generally in the liquid phase) is a preferred step at this point, with detection occurring on the liquid phase.

In the second method of the invention, the sample polynucleotide sought to be detected has two nucleotide sequences sought to be detected: the first target nucleotide sequence ($TNS_1$) and the second target nucleotide sequence ($TNS_2$) (which is the selected nucleotide sequence in the overall description of the reagent complex). It is further sought to detect $TNS_1$ and $TNS_2$ within the same sample polynucleotide rather than within separate sample polynucleotides (such differences being significant in detecting chromosome rearrangements, for example). Provided that the reagent complex is in large molar excess relative to anticipated levels of each target nucleotide sequence (e.g., at least 100:1), probability will favor total displacement if and only if $TNS_1$ and $TNS_2$ are on the same sample polynucleotide strand. Consider first a 100:1 ratio of reagent complexes to sample polynucleotide strands having both $TNS_1$ and $TNS_2$. If $TNS_1$ binds first, then 1% of the reagent complexes can bind $TNS_1$ and displace the signal strand SS from $TBR_1$ (see FIGS. 4C and 5B, below). Because of proximity now of the $TNS_2$ to $TBR_2$ of the same reagent complex molecule, complete displacement of the signal strand is likely to occur. Therefore close to 1% of the reagent complexes will produce a displaced signal strand and, therefore, a detectable sample.

By contrast, if the same reagent complex were contacted with each of $TNS_1$ and $TNS_2$ on separate sample polynucleotide strands at the same 100:1 ratio, then 1% of the reagent complexes would be expected to bind $TNS_1$ and an independent 1% to bind $TNS_2$. Only those reagent complexes, 1/100 of 1%, or 0.01%, would bind both $TBR_1$ and $TBR_2$ and thus have a completely displaced signal strand. Accordingly, the second method can easily distinguish $TNS_1$ and $TNS_2$ on separate sample polynucleotides from $TNS_1$ and $TNS_2$ on the same sample polynucleotide strand. In many cases it is desirable to perform the second method on one aliquot of a sample after having first determined the amount of $TNS_1$ and of $TNS_2$ (without regard to position) on a different aliquot or aliquots by the method of application U.S. Ser. No. 607,885, using separate reagent complexes to determine each.

One can further distinguish the two cases ($TNS_1$ and $TNS_2$ on the same strand compared to $TNS_1$ and $TNS_2$ on separate strands) by subsequently adding a polynucleotide reagent complementary to only $TNS_1$ or to only $TNS_2$. As in the first method of the invention, such reagent polynucleotide will cause completed displacement of labeled polynucleotide which were partly displaced by only $TNS_2$ or only $TNS_1$, respectively, which were present on isolated polynucleotide strands. Such test strategies or protocols, with several variations, are described in more detail below.

The probe polynucleotide used in the reagent complex and methods of the present invention are similar to that described in U.S. Ser. Nos. 607,885, 684,305 and 684,308, except that two or more target binding regions are present. Each target binding region is complementary to a target or selected nucleotide sequence in the sense of perfect or near-perfect complementary base pairing. The size of each target binding region can be thought of as the sum of a labeled polynucleotide binding region (generally at least 15 nucleotides, preferably at least 20 nucleotides, more preferably at least 25 nucleotides, with preferred ranges of 20–1000, 20–500 and 25–200 nucleotides) and a initial binding region (generally at least 15 nucleotides, preferably at least 50 nucleotides, with a preferred range of 50-500 nucleotides). Preferably, the only regions of labeled polynucleotide/-probe polynucleotide complementary base pairing lie within a target binding region; however, a relatively small region (e.g., 5-10 base pairs) may lie outside any target binding region as in FIG. 1G of U.S. Ser. No. 607,885.

The two (or more) target binding fegions within the probe polynucleotide can be immediately adjacent or can be separated by a small or large region of heterologous nucleotides. For the first method of the invention, it is generally preferred that an intervening heterologous region of at least 5 and preferably at least 30 nucleotides be present to minimize steric hindrance when the reagent polynucleotide is hybridizing to the second target binding region or is completing displacement of the labeled polynucleotide from the second target binding region. Intervening heterologous sequences of greater than 1000 nucleotides are of no material increased value, but are permissible. For the second method of the invention, an intervening heterologous sequence may be preferably present in the probe polynucleotide between the first and second target binding regions. The preferred length of such intervening heterologous region is dependent, in part, on the expected spacing between target and selected binding regions when they are within a common sample nucleic acid strand. Intervening heterologous sequences in probe polynucleotide for the second method are preferably at least 5, and more preferably at least 30 nucleotides in length, if the expected spacing between the target nucleotide sequence and the selected nucleotide sequence on a common sample polynucleotide strand is variable. If the target nucleotide sequence and selected nucleotide sequence are expected to be immediately adjacent to each other in only one orientation on a common sample polynucleotide strand, then such spacing between target binding regions is frequently absent.

The positions of the two target nucleotide sequences in the probe polynucleotide relative to anticipated order of target and selected nucleotide sequences in sample strands is not critical, since either corresponding or reversed orders can be sensed, as long as both target binding regions sense the same strand in the target nucleic acid (see FIGS. 5C and 5D, below.)

In many forms of the present invention, the probe polynucleotide is either immobilized or immobilizable in the reagent complex. Exemplary techniques for immobilizing the probe polynucleotide in forming the reagent complex include covalent attachment (see, e.g., the techniques described in U.S. Ser. No. 729,700 of E. Brown, et al., filed May 2, 1985, copending and commonly assigned), attachment via biotin-avidin (as in EPA No. 139,489) and various forms of covalent and non-covalent attachment as described in U.S. Ser. No. 607,885. Exemplary moieties on the probe polynucleotide in the reagent complex, which moieties serve as points of postdisplacement attachment, include biotin attached chemically or biochemically and include the homopolymeric tails of U.S. Ser. No. 729,501 of P. D. Unger et al., filed May 2, 1985 and assigned to Allied Corporation.

The labeled polynucleotide (or signal strand) used in the present invention is similar to that described in earlier applications, including above-referenced 607,885, 684,305 and 684,308, as well as U.S. Ser. No. 729,503, described below, except that at least two pairing segments (each bound in the reagent complex by complementary base pairing to at least part of each target binding region) are present. In particular, tags used may be as described in those applications. The two pairing segments can be immediately adjacent to one another; but, for ease of cloning or for avoiding steric hindrance in forming the reagent complexes and in displacement, or both, it is generally preferred to provide a heterologous intervening sequence in the labeled polynucleotide between the two (or each adjacent pair of) pairing segments. Tags may be attached or present within the intervening sequence, but are preferably adjacent to an end of the labeled polynucleotide exterior to the pairing segments.

Further details of the reagent complexes of the present invention can be understood by the following description of the methods of the present invention.

In the first method of the present invention, one target nucleotide sequence (arbitrarily assigned as complementary to the first target binding region) is a sequence of DNA or RNA which one desires to detect or determine, qualitatively or quantitatively, in a biological sample: e.g., a sequence which is unique and representative of an infectious viral or bacterial genome, a sequence which is unique and representative of a genetic condition or disease state or the like. The second target nucleotide sequence is provided to be noncomplementary with anticipated sequences in the sample to the extent that no sample sequence is expected to be capable of displacing the labeled polynucleotide from the pairing segment of the second target binding region. In such event, the reagent complex is contacted with the sample under conditions in which the target nucleotide sequence, if present, will displace labeled polynucleotide from the first target binding region, but not from the second target binding region. Such conditions can include the temperatures and agents described in U.S. Ser. No. 607,885, 684,305 and 684,308: e.g., 50°-85° C. and no additive or a volume exclusion polymer such as poly(ethylene oxide) (or PEO), or 30°-45°0 C. and a recombination protein (with its co-factors) such as rec A protein from E. coli. For this first method, there are no special constraints upon reagent complex concentration in the reaction mixture (most preferably it is as concentrated as is feasible) or upon the molar ratio of reagent complex to anticipated levels of target nucleotide sequence (although the reagent complex would normally be provided in some excess). This first contacting step can be conducted with an immobilized reagent complex (i.e., one with an immobilized probe polynucleotide) or with a reagent complex in solution.

After the first contacting or displacement step, the reagent complex is washed. For such washing, the reagent complex, if not already immobilized, is preferably immobilized after the first displacement step, such as by passage through an avidin or steptavidin column to immobilize via biotin moieties on the probe polynucleotide. The washing step removes sample materials (both low molecular weight materials and non-target polynucleotides), reagent fragments (e.g., dissociated labeled polynucleotide or fragment thereof), dissociated or poorly-bound reagent complexes, as well as other polymers such as proteins, while retaining the target nucleotide sequences bound by complementary base pairing to the first target binding region.

Thereafter, the washed reagent complex is contacted by a molar excess (preferably at least 2-fold, commonly at least 10-fold) of a reagent polynucleotide which is complementary (perfectly or nearly so) to the second target nucleotide sequence. This second contacting or displacement step can be performed under conditions (including temperature, ionic strength and additives such as PEO or rec A protein or pH or buffer system) conducive to displacing the labeled polynucleotide from the second target binding region and conducive to subsequent steps. In particular, since extraneous sample materials have been removed, greater control can be exerted in conditions for such second displacement (which generally does involve an immobilized probe) than may be possible for the first displacement (which can be in solution where kinetics and steric factors may be more favorable). It is desirable to displace all, nearly all or at least most labeled polynucleotide molecules from corresponding second target binding regions in this second contacting step so that all, nearly all or most of the labeled polynucleotide molecules displaced partially in the first contacting step can now become fully displaced. In most forms of the first method, the fully-displaced labeled polynucleotides are now separated in a liquid phase from the intact or partially intact reagent complexes (containing bound labeled polynucleotides) and are then determined. It is contemplated, however, that in some forms of the invention, homogeneous detection without further separation (e.g., based on fluorescence and quenching as in FIGS. 3A, 3B, 3C and 4 of U.S. Ser. No. 607,885) may be employed.

The choice of any particular tag and read-out procedure is not critical to the present invention; however, the benefits of the first method of the present invention are particularly realized with those tags and read-out procedures deleteriously affected by sample materials normally present with the target nucleic acid. For example, in the procedures of Application U.S. Ser. No. 729,503 of C. Vary, et al., filed May 2, 1985, after displacement, a ribonucleotide segment is digested to nucleoside phosphates (e.g., ADP) which are phosphorylated, followed by detection (e.g., of the ATP produced). Such procedures are sensitive to non-specific signal due to endogenous ADP, endogenous ATP and endogenous digestable RNA (e.g., mRNA having poly A tails) in the sample. While it may be possible to reduce such levels of ADP, ATP and mRNA prior to displacement (as described in U.S. Ser. No. 729,503), the present invention offers the alternative of leaving such materials in the sample and, thus, in the reaction mixture during displacement. By washing after the first displacement step, however, such materials can be removed to insignificant levels; after the washing step, the reagent complex/sample hybrid (generally on a solid phase) can be contacted with a concentrated, contaminant-free solution of the polynucleotide reagent containing the selected nucleotide sequence. The signal strand is then released into a concentrated, contaminant-free solution which can be designed to be ideal for the digestion, phosphorylation and detection steps. Such solution can be designed for freedom from contaminants, for relatively high concentration of displaced signal strands and for factors such as pH, buffer type (e.g., Tris buffer changed to phosphate buffer or vice versa) and ion concentration relevant to these subsequent enzymatic steps, insofar as such conditions still permit hybridization of the reagent polynucleotide having selected nucleotide sequence and subsequent displacement of the labeled polynucleotide.

In similar fashion, enzyme tags on the signal strand can be released, after washing, into a solution of controlled pH, ion concentration and overall concentration, enabling more efficient and more reproducible enzymatic reaction than in displacement assays where such signal strands are displaced into a solution constituted largely of the sample (including materials such as guanidinium thiocyanate which may have been used in sample preparation). Other tags and readouts that can be assisted by such control of the liquid phase into which the signal strand is released include fluorescent tags (detected spectrophotometrically), and luminescence (detected spectrophorometrically).

As discussed briefly above, the second method of the present invention provides information about the extent of nucleic acid strands (DNA or RNA) in a sample with two (or more) defined nucleic acid sequences (called the target nucleotide sequence and the selected nucleotide sequence) in a common strand. Such information is additional to and can be combined with information about the total amount or concentration of either sequence in the sample as measure by the first method of the present invention or by other forms of the basic displacement assay of U.S. Ser. No. 607,885 or by other types of assays. For simplicity, the procedure first described will assume that the absolute amount or concentration of target nucleotide sequences and selected nucleotide sequences are known, at least approximately, and that it is desired to know what proportion are on common polynucleotide strands.

To maximize the detectable difference caused by the two sequences on common strands, it is preferred to use a large molar excess of reagent complexes to anticipated level of either sequence (target nucleotide sequence and selected nucleotide sequence). It is also preferred to not exceed some empirically determined maximum concentration of reagent complexes or density of reagent complexes on a solid support so as to minimize bridging of a sample strand having both sequences between the first target binding region of one reagent complex molecule and the second target binding region of a second reagent complex molecule, which bridging leads to no fully-displaced labeled polynucleotide.

An illustrative case involving translocation of a selected nucleotide sequence to a chromosomal location adjacent to the target nucleotide sequence in a sample illustrates the above principles. Assume that 1 out of 1000 selected nucleotide sequence molecules have been so translocated (for example in a pre-cancerous condition in, for example, human white blood cells). Knowing the total concentration of selected nucleotide sequences, one could employ a 100:1, 1000:1, or 10,000:1 molar ratio of reagent complexes (having first and second target binding regions) relative to selected nucleotide sequences. Assume next that the amounts of target nucleotide sequences and selected nucleotide sequences are equal. Then the following proportions of label should be totally displaced on account of the non-translocated selected nucleotide sequences (on separate sample strands from the target nucleotide sequences) and on account of the translocated selected nucleotide sequences (on common sample strands with the target nucleotide sequences):

| | For Each 1 Translocated strand: $10^3$ Non-translocated Strands | |
|---|---|---|
| Reagent Complex | Signal Events On Account Of | |
| Molecules | Non-Trans | Trans |
| $10^5$ (100:1) | 10 | 1 |
| $10^6$ (1000:1) | 1 | 1 |

| | -continued | |
|---|---|---|
| | For Each 1 Translocated strand: 10³ Non-translocated Strands | |
| Reagent Complex Molecules | Signal Events On Account Of | |
| | Non-Trans | Trans |
| 10⁷ (10,000:1) | 0.1 | 1 |

Thus, to detect 1 of 1000 translocations as a significant change in signal, at least a 1000:1 molar ratio, and preferably at least a 10,000:1 molar ratio of reagent complexes to total selected nucleotide strands is required. If the minimum signal detectable is $10^3$ displaced labeled polynucleotides, then $10^3$ translocated strands in a population of $10^6$ selected nucleotide sequences can be detected using $10^{10}$ reagent complex molecules (or $1.7 \times 10^{-14}$ mole or 0.017 pmole). Such reaction would be expected to occur in a reaction volume of one milliliter such that the final reagent complex concentration would be 0.017 pmol/ml or $1.7 \times 10^{-11}$ molar. It is anticipated that such a concentration of reagent complexes is sufficiently low that the vast majority of the $10^3$ sample strands present having target nucleotide sequence and selected nucleotide sequence would totally displace labeled polynucleotide strands from individual reagent complex molecules rather than bridging the first target binding region and second target binding region of separate reagent complex molecules. See J. G. Wetmur, N. Davidson, *J. Mol. Biol.*, vol. 31, pp. 349-370 (1968); A. Dugai czyk, H. W. Boyer & H. M. Goodman, *J. Mol. Biol.*, vol. 96, pp. 171-184 (1975).

The additional information provided by the second method of the invention can be significant for a variety of clinical and other applications with a variety of target sequence pairs: target nucleotide sequence and selected nucleotide sequence. Examples for DNA include chromosomal translocations of two types, either of which may have significance to cancer or pre-cancerous conditions. In the first condition, the target nucleotide sequence is normally present at a remote location (i.e., a separate chromosome) from the selected nucleotide sequence. An example taken from C.M. Croce and G. Klein, "Chromosome Translocations And Human Cancer", *Scientific American* vol. 252, no. 3, pp. 54-60 (March 1985) is the translocation between human chromosomes 8 and 14 (illustrated on page 56). One could choose as the target nucleotide sequence a sequence present on chromosome 8 near the location where translocation (actual exchange of chromosome fragments) occurs. The selected nucleotide sequence would be a sequence present normally on chromosome 14 that, in the event of translocation, is found on modified chromosome t(8,14) along with the target nucleotide sequence. The two sequences could be sequences having presumed functional significance in the disease (i.e., the oncogene c-myc and the immunoglobulin heavy chain gene in Burkitt's lymphoma); but the target nucleotide sequence could as well be sequences of no function or of unknown function that become juxtaposed in the event of translocation. In selecting sequences to target, relative uniqueness can be a more significant factor than functionality.

The second method of the invention can also be used in the situation where the target nucleotide sequence and selected nucleotide sequence are normally present together, but are separated in the event of a translocation. For example, the c-myc gene could be the target nucleotide sequence, and a DNA sequence which normally is present 3' to the c-myc gene could be the selected nucleotide sequence. Translocations which result in loss of this 3' selected nucleotide sequence from chromosome 8, i.e., such as translocations between 8 and 2 or 8 and 22 in Burkitts lymphoma, could then be detected. In this case, a two step process is required. Clinical sample is first reacted with reagent complex, and analytes with unrearranged sequences will mediate complete displacement. This reaction could then be analyzed to determine the number of unrearranged chromosomes detected. To subsequently detect the presence of rearranged sequences, a reagent polynucleotide containing the selected nucleotide sequence would then be added. Complete displacement would then occur from those reagent complexes which had only hybridized to target nucleotide sequences present in a single sample polynucleotide strand. Quantitation of liquid phase after this second displacement reaction would allow an estimate of the percent of rearranged DNA molecules, without requiring a reagent complex specific for either chromosome 8 or chromosome 22.

The present second method can further be used for detecting changes in a DNA sequence as may occur during cell diffentiation: e.g., changes in the sequence coding for a light or heavy chain of an antibody. While the variable region of interest may be detected by, e.g., the method of U.S. Ser. No. 607,885, its proximity to a particular relatively non-variable region can be determined by the second method of the present invention.

In each of the above instances, it is important to note that the length of intervening sequence of the region of the sample nucleotide strand having both a target nucleotide sequence and a selected nucleotide sequence is relatively unimportant, and will not substantially affect the signal produced. This enables, for example, translocations to be assayed without regard to the particular break point between regions of DNA translocated and regions of DNA remaining in the original chromosomes. In general, however, as the length of intervening sequence in the sample polynucleotide increases, the likelihood of selected nucleotide sequence and target nucleotide sequence both hybridizing to the same probe strand decreases, and the probability of their hybridizing to different probe strands increases. If the intervening sequence is particularly long, however, some care may be required in sample preparation to assure that chromosomal DNA strands having both sequences are sufficiently intact at the time of the displacement step to be detectable as such.

In some forms of the invention, e.g., because of expected heterogeneity in chromosomal break points for a single disease, a plurality of reagent complexes are used, either: (1) in separate reaction or (2) in the same reaction, but with distinguishable tags in some cases. If two reagent complexes are targeted against the same selected nucleotide sequence (sequence B), but against different target nucleotide sequences (sequences A and C), then complete displacement from both strands is indicative of sequence A and B on some common sample strands and B and C on some common sample strands. Under certain circumstances, this may indicate that sequences A and C are on the same strand in an organism, even though they are spaced too far apart to remain on the same strand after the random cleavage that may occur during sample preparation, or are too spaced apart to displace specifically a labeled polynucleotide from target nucleotide sequence A' and C' complementary to sequences A and C, respectively. If, however, sequence B is known to remain with sequence C, then only the reagent complex targeted for A and B is required.

The present second method also applies to target and selected nucleotide sequences as RNA, including rRNA, mRNA and tRNA, but especially as mRNA. There may be instances, for example, of two sequences in close proximity as DNA which, in some translocational (or transcriptional) states, produce complementary mRNA sequences in a common mRNA strand and, in other translocational (or transcriptional) states, do not. Such differences could result from either genetic change or regulatory change. Furthermore, as illustrated in articles concerning the 37 Philadelphia Chromosome38, translocations (involving the c-abl locus of human chromosome 9 being translocated near the bcr locus of human chromosome 22, correlated with a leukemia condition) changes at the DNA level (see N. Heisterkamp, et al., *Nature, vol.* 306) 239-277 (1983) and Groffen, et al., *Cell,* vol. 36, pp. 93-99 (1984) are sometimes transcribed into fused RNA sequences (E. Shtivelman, et al., *Nature,* vol. 315, pp. 550-554 (1985). In such cases detection of mRNA has the advantages of:

1. sample strands found in multiple copy number per cell and in single-stranded form;
2. sample strands having potentially smaller, less variable or no intervening nucleotide sequence in mRNA relative to DNA (because of the non-transcription of introns); and
3. the possibility of focusing on translocations of functional significance to certain cancers.

A review of rearrangements in cancer is J. J. Yunis, *Science,* vol. 221, pp. 227-36 (1983), wherein it is estimated that chromosomal abnormalities are present in 98% of cancers and that the Philadelphia Chromo is present in about 90% of chronic myelocytic leukemia cases. Examples of translocations associated with specific neoplasmas are the following, the first two of which are well-characterized:

1. CML: t(9;22);
2. Burkitt's Lymphoma: t(8;14), t(8;2) or t(8;22);
3. Non-Hodgkins Lymphoma: t(18;14) or t(8;14) (see Yunis, et al., *New Eng. J. Med.,* vol. 307, pp. 1231-1236 (1982);
4. AML (M2 subtype): t(8,21) (correlated with about 10% of the M2 type of Acute Myeloblastic Leukemia)*;
5. Acute Promyelocytic Leukemia: t(15;17)*;
6. AML (M4 subtype): inv (16) (p13q22)*;
7. Acute Lymphocytic Leukemia: t(4;11) or t(9;22) or t(8;14)*;
8. Small cell Carcinoma of Lung: del (3p21p23)**;
9 Ovarian Papillary Cystadenocarcinoma t(6;14)**.

* M. Pearson & J. D. Rowley, *Ann. Rev. Med.,* vol. 36, pp. 471-483 (1985),
** above-cited Yunis 1983 review article.

Compared to methods involving the detection merely of the presence of a single sequence, the present proximity analysis can be used as an initial diagnostic or screening test or as a test to follow the numbers of malignant or pre-malignant cells with a specific rearrangement in patients during or after therapy or in remission. The method (especially with mRNA targeted) is simpler than karyotyping and can be applied to non-dividing cells (e.g., peripheral blood cells rather than bone marrow cells).

In addition to translocation of chromosomal DNA and eukaryotic mRNA, translocations in bacterial, viral or other procaryotic DNA and RNA can be detected by similar techniques and reagent complexes. Such translocations may have significance in terms of identification of microorganisms or providing additional information about the control regimes, drug resistances or virulence of a microorganism, or location of a particular target sequence in a particular plasmid. The method of the present invention can also be used to monitor sequence positioning in the development, amplification, maintenance against deleterious mutation and quality control of genetically engineered microorganisms.

FIG. 1A illustrates a reagent complex according to a first embodiment of the present invention. The probe polynucleotide P is immobilized at one end to a support SU and contains a first target binding region $TBR_S$ and a second target binding region $TBR_R$ complementary to, respectively, the target nucleotide sequence to be detected in the sample and a reagent nucleotide sequence to be added in the third step of the method. The two target binding regions are separate in the probe by an intervening sequence $IS_P$. A signal strand or labeled polynucleotide SS contains a detectable tag T at a free end and is bound by complementary base pairing to portions $LBR_S$ and $LBR_R$ of target binding regions $TBR_S$ and $RS_R$, respectively. The two pairing segments $PS_S$ and $PS_R$ are separated in the labeled polynucleotide SS by an intervening sequence $IS_L$. The other portions, initial binding region $IBR_S$ and $IBR_R$ of target binding regions $TBR_S$ and $TBR_R$, respectively, are single-stranded.

In the first contacting step of the first present method, such a reagent complex as shown in FIG. 1A is contacted by a sample. If such sample contains the target binding region (complementary to $TBR_S$), then nucleation can occur in $IBR_S$ followed by displacement of the labeled polynucleotide SS (and especially pairing segment $PS_S$) from $LBR_S$ by mechanisms described in U.S. Ser. No. 607,885.

Figure 1B:
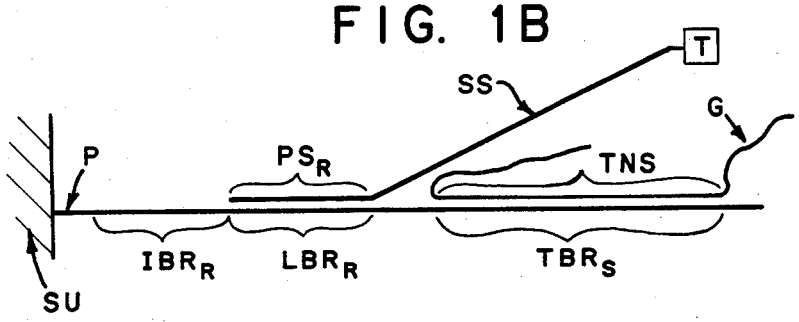

FIG. 1B illustrates the intermediate structure that can thus form for each sample nucleic acid strand G that includes a target nucleotide sequence TNS. In such structure, the target nucleotide sequence TNS is bound by complementary base pairing to $TBR_S$, but the labeled polynucleotide SS remains attached to the probe P and (indirectly) the support SU via $PS_R$ bound to $LBR_R$.

At this point the solid phase (anything attached to support SU) is washed to remove extraneous sample material or materials associated with providing the sample strand G in single-stranded form.

Figure 1C:
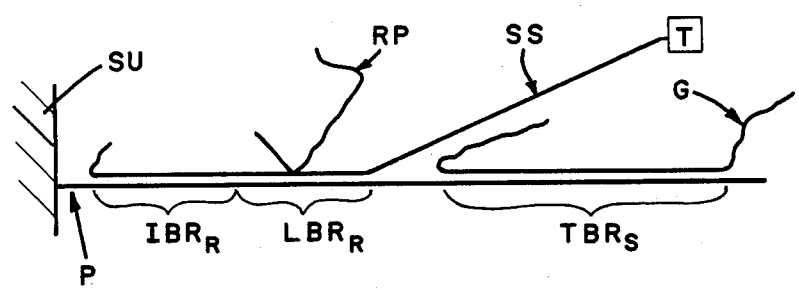
Figure 1D:
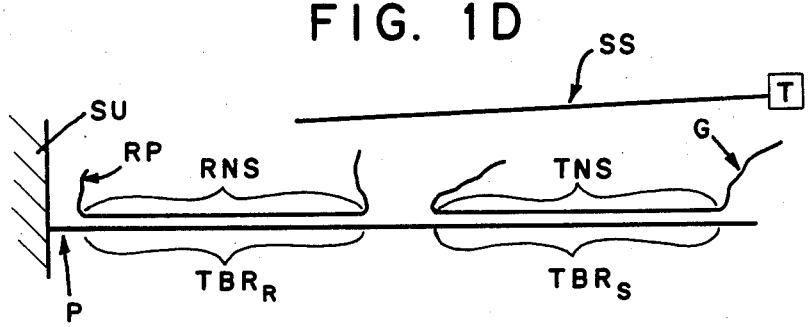

A reagent nucleotide sequence RP is then introduced, preferably in molar excess. It binds to $IBR_R$ and then displaces the labeled nucleotide sequence SS from $LBR_R$. FIG. 1C illustrates an intermediate stage in such displacement. For strands in which the labeled polynucleotide has already been displaced from $TBR_S$ by target nucleotide sequence TNS, the displacement by reagent nucleotide sequence RP will completely separate the labeled polynucleotide SS from the probe polynucleotide P as shown in FIG. 1D. Upon separating the liquid phase from the support SU, the tag T in the liquid phase can be detected in an amount functionally related to the amount or concentration of target nucleotide sequence TNS in the sample. Labeled polynucleotide strands SS of reagent complexes which have been contacted only by reagent polynucleotide RP, and not by target nucleotide sequence TNS, will remain with the solid phase because of attachment of $PS_S$ to $LBR_S$.

Figure 2A:
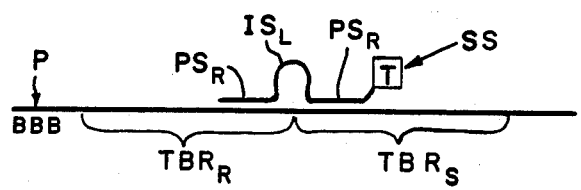
FIG. 2, in three parts, is a schematic view of a second embodiment of the present invention, in which a reagent complex (FIG. 2A) is contacted with a sample polynucleotide G (in FIG. 2B) and then a reagent polynucleotide RP (in FIG. 2C) to displace a signal strand SS in accordance with the first method of the present invention.

FIG. 2 illustrates an embodiment of reagent complex and first method differing from that of FIG. 1 in that the probe polynucleotide P is immobilizable rather than immobilized. FIG. 2A illustrates a reagent complex according to a second embodiment of the present invention. The probe polynucleotide P has a biotinylated tail (shown as Bs) on one end (e.g., 3′ poly (biotinyl-dU formed by TdT extension) and contains a first target binding region $TBR_S$ and a second target binding region $TBR_R$ complementary to, respectively, the target nucleotide sequence to be detected in the sample and a reagent nucleotide sequence to be added in the third step of the method. The two target binding regions are immediately adjacent to each other.

A signal strand or labeled polynucleotide SS contains a detectable tag T at a free end and is bound by complementary base pairing to portions of target binding regions $TBR_S$ and $TBR_R$, as in the first embodiment. The two pairing segments $PS_S$ and $PS_R$ are separated in the labeled polynucleotide SS by an intervening sequence $IS_L$. Other portions (shown as initial binding region $IBR_S$ and $IBR_R$ in FIG. 1A) of target binding regions $TBR_S$ and $TBR_R$, respectively, are single-stranded.

In the first contacting step of the present method, such a reagent complex as shown in FIG. 2A is contacted in solution by a sample. If such sample contains the target binding region (complementary to $TBR_S$), then nucleation can occur in $IBR_S$ followed by displacement of the labeled polynucleotide SS (and especially pairing segment $PS_S$) from $LBR_S$ by mechanisms described in U.S. Ser. No. 607,885. At this point, probe strands P can be immobilized by passing the reaction mixture through a streptavidin column.

Figure 2B:
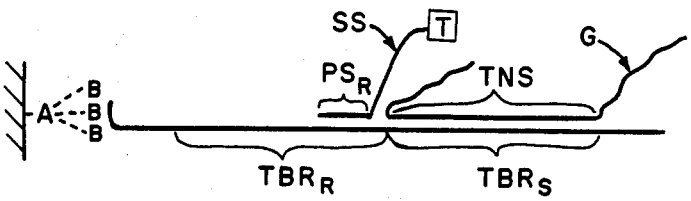

FIG. 2B illustrates the intermediate structure that can thus form for each sample nucleic acid strand G that includes a target nucleotide sequence TNS. Each probe polynucleotide is bound to a support SU by the binding of its biotinylated tail B to streptavidin molecules A on the support SU. In such structure, the target nucleotide sequence TNS is bound by complementary base pairing to TBR, but the labeled polynucleotide SS remains attached to the probe P and (indirectly) the support SU via $PS_R$ bound to $LBR_R$ of the probe P and via the biotinylated tail B of probe P bound to streptavidin A on the support SU.

At this point the solid phase (anything attached to support SU) is washed to remove extraneous sample material or materials associated with providing the sample strand G in single-stranded form.

Figure 2C:
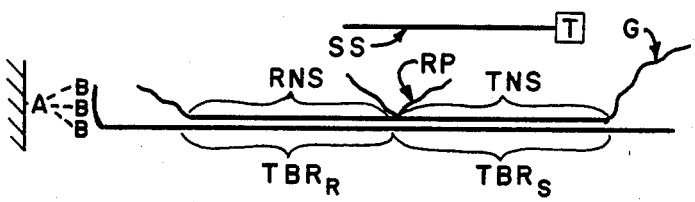

A reagent nucleotide sequence RP is then introduced, preferably in molar excess. It binds to $IBR_R$ and then displaces the labeled nucleotide sequence SS from $LBR_R$. An intermediate stage in such displacement (similar to that of FIG. 1C) now forms. For strands in which the labeled polynucleotide has already been displaced from $TBR_S$ by target nucleotide sequence TNS, the displacement by reagent nucleotide sequence RP will completely separate the labeled polynucleotide from the probe polynucleotide P as shown in FIG. 2C. Upon separating the liquid phase from the support SU, the tag T in the liquid phase can be detected in an amount functionally related to the amount or concentration of target nucleotide sequence TNS in the sample. Labeled polynucleotide strands SS of reagent complexes which have been contacted only by reagent polynucleotide RP, and not by target nucleotide sequence TNS, will remain with the solid phase because of attachment of $PS_S$ to $LBR_S$.

Figure 3A:
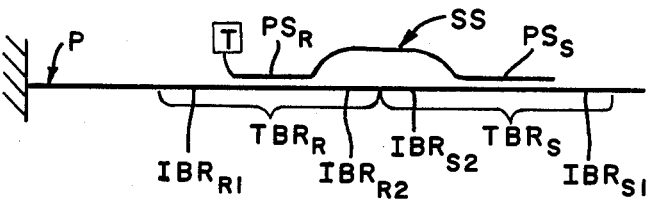
FIG. 3A is a schematic view of a third embodiment of the reagent complex of the present invention.

FIG. 3A illustrates a third embodiment of the reagent complex of the present invention. It differs from the first embodiment shown in FIG. 1A ln that pairing segments $PS_R$ and $PS_S$ (of labeled polynucleotide SS) are bound to intermediate rather than end portions of target binding regions $TBR_R$ and $TBR_S$, respectively. Therefore, each target binding region has two initial binding regions: $IBR_{R1}$ and $IBR_{R2}$ of $TBR_R$ and $IBR_{S1}$ and $IBR_{S2}$ of $TBR_S$. As in the second embodiment of FIG. 2A, no intervening segment separates $TBR_R$ from $TBR_S$ in probe P.

Figure 3B:
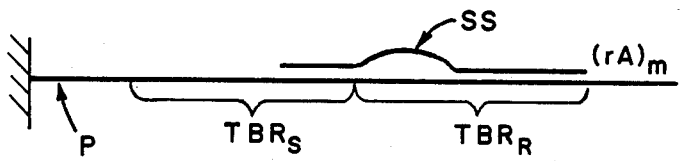
FIG. 3B is a schematic view of a fourth embodiment of the reagent complex of the present invention.

FIG. 3B illustrates a fourth embodiment of the reagent complex of the invention wherein the tag is a terminal polyriboadenosine segment as in U.S. Ser. No. 729,503 of Vary, et al. The labeled polynucleotide SS is bound to end portions, but not adjacent end portions, of the target binding regions $TBR_S$ and $TBR_R$.

Figure 3C:
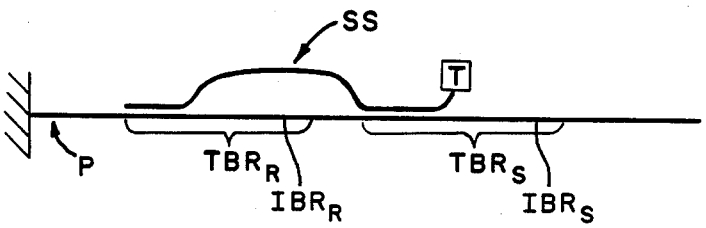
FIG. 3C is a schematic view of a fifth embodiment of the reagent complex of the present invention.

FIG. 3C illustrates a fifth embodiment of the reagent complex of the invention wherein the labeled polynucleotide SS is bound to end portions of $TBR_R$ and $TBR_S$ closest along probe P to support SU. Furthermore, unlike the first embodiment FIG. 1A, $TBR_R$ is closer to support SU than is $TBR_S$.

Figure 3D:
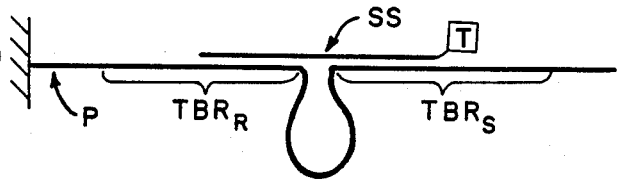
FIG. 3D is a schematic view of a sixth embodiment of the reagent complex of the present invention.

FIG. 3D illustrates a sixth embodiment of the reagent complex of the invention with $TBR_R$ closer to support SU than is $TBR_S$, and with an intervening sequence between $TBR_S$ and $TBR_R$ (like $IS_p$ in FIG. 1A) much larger than the intervening sequence between the pairing segment of labeled polynucleotide SS (like $IS_L$ in FIG. 1A).

Figure 4A:
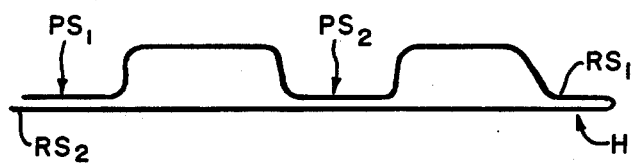
FIG. 4 is a schematic view, in three parts, of a seventh embodiment of the present invention, showing, in FIG. 4B, the reagent complex and, in FIG. 4A, a precursor nucleic acid construct therefore (based upon our U.S. Ser. No. 729,504, filed May 2, 1985).
FIG. 4C illustrates the second method of the present invention wherein the reagent complex is contacted with a sample polynucleotide G containing both target nucleotide sequence $TNS_1$ and $TNS_2$.
Figure 4B:
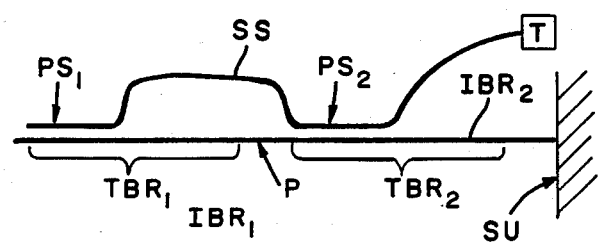

FIG. 4B illustrates a seventh embodiment of the reagent complex of the present invention. Here, the two target binding regions are identified as $TBR_1$ and $TBR_2$ (each complementary to a sequence to be detected: the target nucleotide sequence $TNS_1$ and the selected nucleotide sequence $TNS_2$ by the second method of the present invention). Pairing segments $PS_1$ and $PS_2$ are bound to end portions of $TBR_1$ and $TBR_2$, respectively, leaving single-stranded initial binding regions $IBR_1$ and $IBR_2$, respectively. An end of the probe P containing $TBR_1$ and $TBR_2$ is bound to support SU; an end of the labeled polynucleotide containing $PS_1$ and $PS_2$ has a detectable tag T.

FIG. 4A illustrated a DNA nucleic acid construct of the type that may be formed in the processes of our U.S. Ser. No. 729,504 within a plasmid or the like, by cloning segments $PS_1$, $PS_2$, $TBR_1$ and $TBR_2$ into appropriate restriction sites in appropriate orientations and cleaving at restriction site $RS_2$ to form the two free ends shown in FIG. 4A. The construct of FIG. 4A can be converted into the reagent complex of FIG. 4B by the process described in U.S. Ser. No. 729,504 (the disclosure of which is incorporated by reference) by steps of cleaving hairpin H at restriction site $RS_1$, attaching tag T to a specific end (e.g., a 3′ end) and attaching the other end (e.g., the 5′ end) to the support SU. Such attachment steps may employ the techniques of U.S. Ser. No. 729,700 of E. Brown, et al., also filed May 2, 1985.

The various reagent complexes described herein may also be formed by hybridizing labeled polynucleotides SS to probe polynucleotides P (formed separately), with attachment of tags T and to supports SU optionally performed before or after hybridization. The techniques of U.S. Ser. No. 729,504 are preferred, however.

In the contacting step of the present second method, such a reagent complex as shown in FIG. 4B is contacted by a sample. If a nucleic acid strand G in such sample contains the target binding region (complementary to $TBR_2$), then nucleation can occur in $IBR_2$ followed by displacement of the labeled polynucleotide SS (and especially pairing segment $PS_2$) from $LBR_2$ by mechanisms described in U.S. Ser. No. 607,885, with results as shown in FIG. 4C.

Figure 4C:
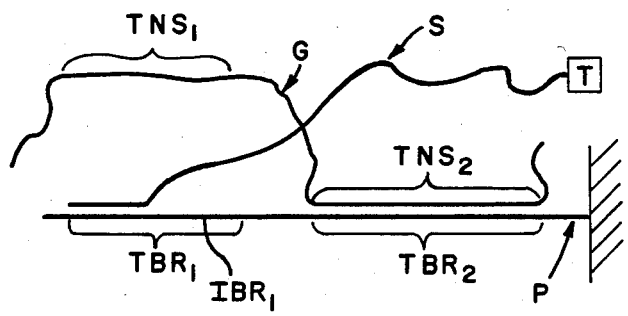

FIG. 4C illustrates the intermediate structure that can thus form for each sample nucleic acid strand G that includes a target nucleotide sequence $TNS_2$. In such structure, the target nucleotide sequence $TNS_2$ is bound by complementary base pairing to $TBR_2$, but the labeled polynucleotide SS remains attached to the probe P and (indirectly) the support SU via $PS_1$ bound to $LBR_1$.

For sample strands having only $TNS_2$, displacement ends at this point, the labeled polynucleotide SS remains attached to support SU and its tag T is not detected on the liquid phase unless a sample strand with $TNS_1$ contacts the same reagent complex molecule (an improbable event under preferred reaction conditions) or a reagent polynucleotide containing $TNS_1$ is added (which would not be done for the initial determination).

Sample strands such as G in FIG. 4C having both $TNS_1$ and $TNS_2$ are likely, however, to undergo further displacement. In such event, $TNS_1$ (shown free in FIG. 4C) can hybridize to $IBR_1$, which is reasonably close, and can then displace the labeled polynucleotide SS from $TBR_1$ (not shown but similar to FIGS. 1D, 2C and 5C). Such event, which is expected to occur quickly and in high yield for such strands G as are present, will result in a totally displaced labeled polynucleotide SS. Separation of a liquid phase from the support SU should isolate such totally-displaced labeled polynucleotides SS. Determination of tags T in such liquid phase would give a value functionally related to the sample strands G having $TNS_1$ and $TNS_2$. If desired, a reagent polynucleotide containing only one $TNS_1$ or only $TNS_2$ can now be added to the solid phase and a second liquid phase produced (according to the first method of the invention). The additional information produced by determining the tags in the second liquid phase may serve both as a control and as a verification of the total level of one sequence (the other of $TNS_1$ and $TNS_2$ not in the reagent polynucleotide employed).

Additionally, as described above for the chromosome 8 sequences, such further information may be used for target and selected nucleotide sequences present together in normal patients, but translocated (e.g., to chromosome 2 or 22) in individuals with a cancerous, pre-cancerous or other clinically-significant condition.

Figure 5A:
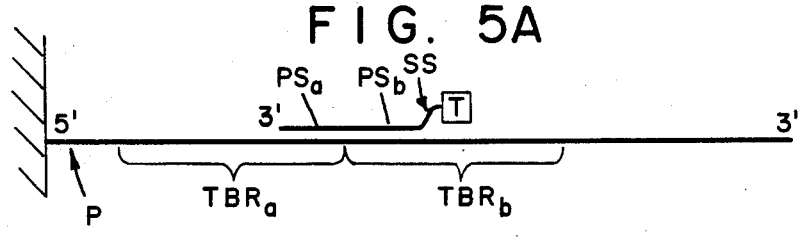
FIG. 5 is a schematic view, in three parts, of a reagent complex in accordance with an eighth embodiment of the present invention (FIG. 5A) used in the second method of the present method.
In FIGS. 5B and 5C a sample polynucleotide G, containing both target binding regions $TNS_a$ and $TNS_b$ displaces a signal strand SS from the reagent complex.
FIG. 5D is a schematic view, similar to FIG. 5C, of the signal strand SS displaced from the reagent complex of FIG. 5A by a sample polynucleotide $G_I$ containing the target nucleotide sequences $TNS_a$ and $TNS_b$ in inverted order compared to sample polynucleotide G.

FIG. 5A illustrates an eighth embodiment of the reagent complex of the present invention used for the second method of the invention. The two target binding regions $TBR_a$ and $TBR_b$ have no intervening sequence between them, nor do pairing segments $PS_a$ and $PS_b$ of labeled polynucleotide SS. The probe is attached at its 5' end to a support SU. The labeled polynucleotide SS has at its 5' end a tag T.

Figure 5B:
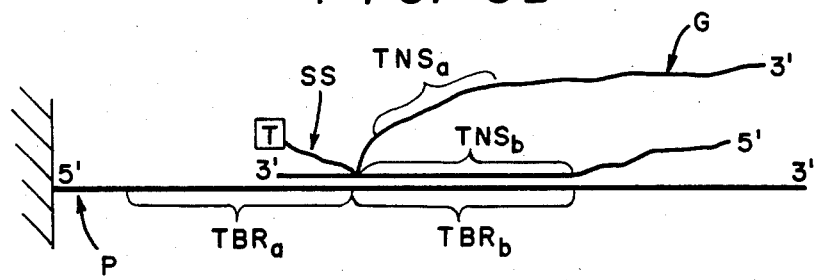
Figure 5C:
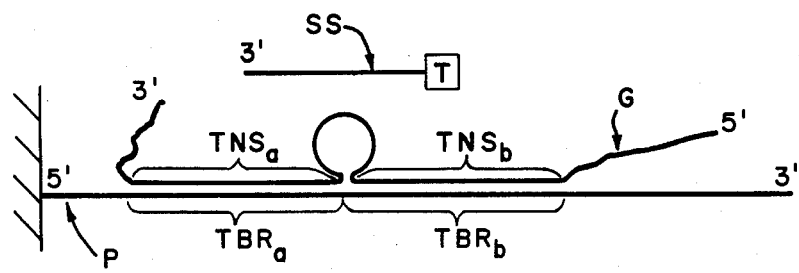

Contact of such a reagent complex by a sample strand G having the target and selected nucleotide sequences in corresponding order proceeds (as illustrated in FIGS. 5B and 5C) through an intermediate stage (in FIG. 5B corresponding to FIG. 4C) and then to a stage (shown in FIG. 5C) wherein the labeled polynucleotide SS is completely displaced.

Figure 5D:
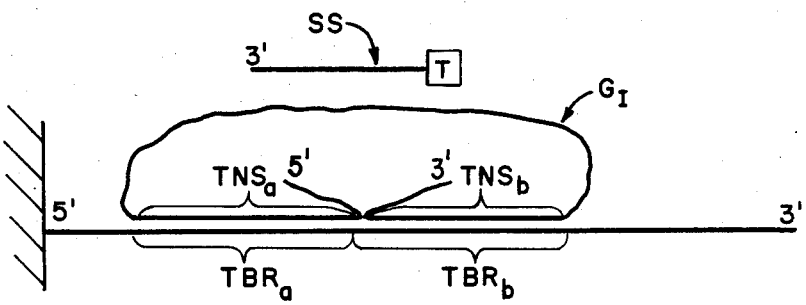

The reagent complex of FIG. 5A can also, however, detect target and selected nucleotide sequences $TNS_a$ and $TNS_b$ in reversed order, as shown by sample strand $G_I$ in FIG. 5D (showing the stage of completed displacement) provided that the intervening sequence in $G_I$ is sufficiently long to span the distance from the exterior ends of $TBR_a$ and $TBR_b$.

It will be appreciated that similar reagent complexes with three or more target binding regions can be constructed and used either for detecting the proximity of three or more nucleotide sequence in a sample polynucleotide strand or for causing a displacement by sequence on a common strand (as in FIG. 5C) from all but one target binding region, then washing, and then displacing from the last target binding region with a reagent polynucleotide.

EXAMPLES

Example 1

Construction Of Probe Polynucleotide

A human albumin cDNA clone identical to the portion of the cDNA described in Lawn, et al., Nucleic Acid Res., vol. 9, pp. 6103–6114 (1981), from the 19th nucleotide of the mature coding region to the 3' end of the mRNA was digested with restriction endonuclease Pst I and the 1071 bp Pst I fragment was cloned into the Pst I site of M13mp7 bacteriophage. The cloned insert was 1071 bp in length, having restriction sites as follows:

| Restriction sites | Position from 5' end |
| --- | --- |
| Pvu II | 156 |
| Hpa II | 463 |
| Bgl II | 693 |
| Bgl II | 730 |
| Xba I | 1050 |
| Pst II | 1071 |

The correct insert was identified by hybridization with the 32-mer 5'-TCCTTTGCCTCAGCA-TAGTTTTTGCAAACATC-3'. The mature strand of this M13 clone is shown as probe $P_2$ in FIG. 6.

Figure 6:
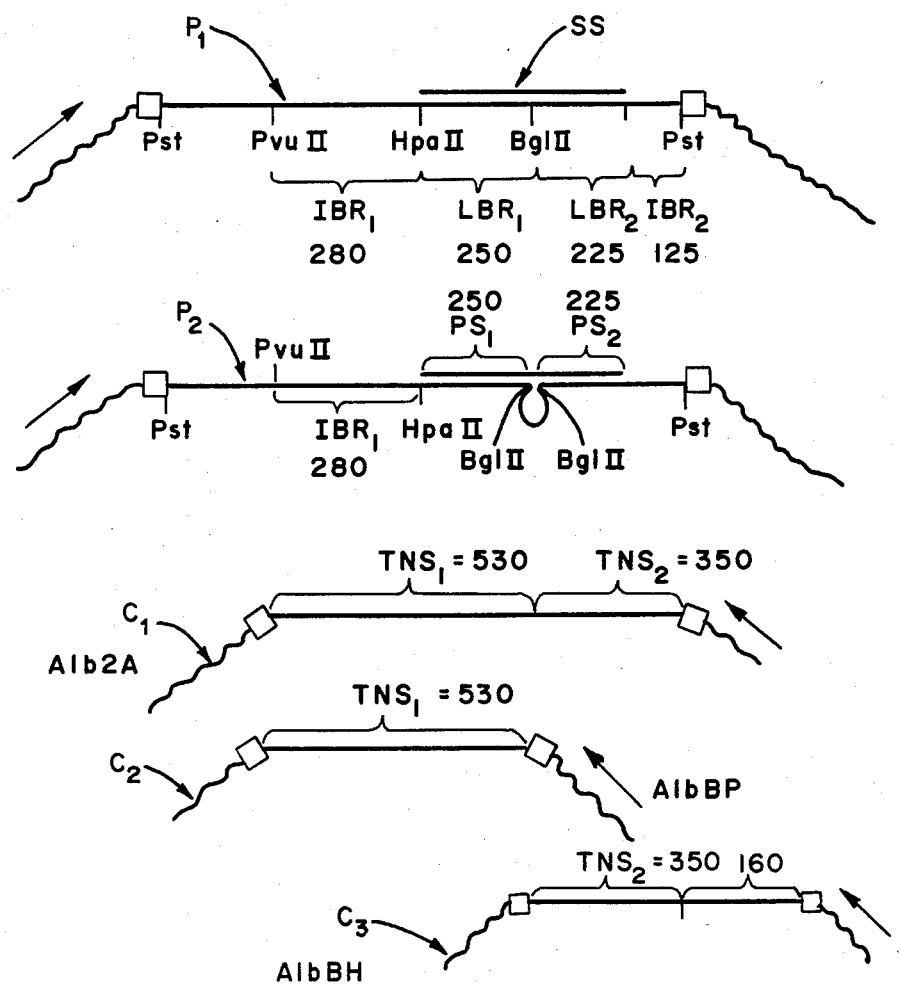
FIG. 6 is a schematic view of the two reagent complexes (containing probes $P_1$ and $P_2$) and the three competitor polynucleotides ($C_1C_2$ and $C_3$) used in Example 1 of the present application.

The small (37 bp) Bgl II fragment in the middle of the above clone was removed by digestion with restriction endonuclease Bgl II, recircularizing and retransforming. The correct clone (probe $P_1$ in FIG. 6 represents its mature single-stranded form) was confirmed by DNA sequence analysis.

Construction of Competitors

The albumin Pvu II - Bgl II fragment (537 bp) was gel isolated and cloned into M13mp9 bacteriophage which had been digested with restriction endonucleases Sma I and Bam HI. The correct fragment and orientation (the mature form being shown in FIG. 6 as competitor $C_2$) were confirmed by restriction endonuclease mapping.

The albumin Hinc II - Bgl II fragment (510 bp, see Lawn, et al.) was gel isolated from an 1100 bp albumin cDNA clone containing this region and cloned into M13mp8 bacteriophage which had been digested with the restriction endonucleases Sma I and Bam HI. The correct fragment and orientation (the mature single-stranded form is illustrated in FIG. 6 as competitor $C_3$) was identified by restriction endonuclease mapping.

The third competitor, shown in FIG. 6 as $C_1$, contained the albumin sequence complementary to DNA polynucleotide $P_2$. The mature single-stranded form contains the complementary sequence to the entire 1071 nucleotide insert of probe $P_2$, and all of the 1034 nucleotide insert of probe $P_1$.

Signal Strand Synthesis

The clone shown in FIG. 6 as probe $P_1$ was used as the template and the 32-mer identified above was used as a primer (i.e., hybridized to the template at a position 193-225 nucleotides 3' to the Bgl II site at position 730). The mixture used was:

1 microgram probe $P_1$
20 picmoles 32-mer
5 microliter alpha 32-p dATP (3000 Ci/mM)
5 microliter 10X seq buffer*
2 microliter 20 micromolar dATP
3.75 microliter 6.6 mM mix of dCTP, dGTP and dTTP
4 units Klenow (DNA polymerase from *E. coli*).

*10 seq buffer is 0.1M Tris HCl (pH 7.5), 0.5 M NaCl, 0.1M DTT and 0.1M MgCl$_2$.

After incubating for 20 minutes at 22° C, 1.2 microliter 20 mM dATP were added, and incubation was continued for 20 minutes at 22° C. After extracting once with phenol/chloroform, unicorporated label was removed by spin column chromatography on Sephadex G-50 (see Maniatis et al., *Cloning Manual*, pp. 466 (1982)). To the mix was added one-tenth volume of a buffer (10X) for Hpa II and then 20-30 units of restriction endonuclease Hpa II (supplied by New England Biolabs, see their catalog for buffer composition). After incubating for 2 hours at 37° C., ethanol precipitating and resuspending (in 50 microliters of 10 mM Tris, pH 8), NaOH was added to 100 mM. After incubation for 10 minutes at 68° C., the sample was loaded on 1.5% alkaline agarose gel (50 mM NaOH, 10 mM EDTA) and electrophoresed to recover the 425 nucleotide radiolabeled fragment, the signal strand SS in FIG. 6.

Preparation of Reagent Complex

The 455 nucleotide sequence strand described above (approximately 6 pmoles) was incubated with 3-4 micrograms (1.5-2 pmoles) of undigested circular probe $P_1$ or undigested circular probe $P_2$ in 1M NaCl, 50 mM Tris, pH8, 10 mM EDTA at 68° C. for 2 hours. Unhybridized signal strand was removed by chromatography on Sepharose Cl-4b.

Displacements

The above reagent complex (about 20-50 ng) was mixed with 60 ng of each of the following competitors (which had been cleaved with endonuclease Hae III for two hours at 37° C.) in 20 microliters of 1M NaCl, 50 mM Tris, pH 8, 10 mM EDTA at 68° C. for the indicated number of minutes. After each displacement, the reaction mixture was subjected to gel electrophoresis (neutral 1.5% agarose gel) and autogradiography. Based upon visual estimates, no displacement occurred for the following competitors and times (with either probe $P_1$ or probe P2):

| Competitor | Time |
|---|---|
| C2 | 60 minutes |
| C2 | 30 minutes |
| C3 | 60 minutes |
| C3 | 30 minutes |

Complete displacement was observed with competitor $C_1$ in either 30 or 60 minutes. When displacements were run with competitor C2 for 30 minutes and then competitor C3 was added and incubation continued for 30 minutes, complete displacement was observed (with either probe $P_1$ or probe P2). The same results were obtained when competitor C3 was used first and competitor C2 second for 60 minutes total incubation time.

Example 2

Example 1 was repeated using the reagent complex having probe $P_1$, incubating for 30 minutes with 3-4 micrograms of one of competitor C2 or C3, then adding 5 micrograms of the other of competitor C2 or C3 and then incubating for two minutes. Complete displacement was observed.

We claim:
1. A reagent complex for the determination of a predetermined target nucleotide sequence in the nucleic acid of a biological sample comprising:
   (a) a probe polynucleotide having:
      (i) a first target binding region which is capable of complementary base pair binding via hydrogen bonds of purine/pyrimidine base pairs to a target nucleotide sequence; and
      (ii) a second target binding region which is capable of complementary base pair binding via hydrogen bonds of purine/pyrmimidine base pairs to a selected nucleotide sequence; and
   (b) a labeled polynucleotide which is bound by complementary base pair binding via hydrogen bonds of purine/pyrimidine base pairs to the probe polynucleotide in at least a portion of the first target binding region and in at least a portion of the second target binding region.

2. The reagent complex of claim 1 wherein the selected nucleotide sequence is present in a biological sample in varying degrees of proximity to the target nucleotide sequence.

3. The reagent complex of claim 2 wherein the target nucleotide sequence and selected nucleotide sequence are chromosomal DNA sequences whose relative position changes with disease states.

4. The reagent complex of claim 3 wherein the target nucleotide sequence and selected nucleotide sequence are normally on separate chromosomes but, in a disease state, are on a common chromosome.

5. The reagent complex of claim 3 wherein the target nucleotide sequence and selected nucleotide sequence are normally on a common chromosome but, in a disease state, are on separate chromosomes.

6. The reagent complex of claim 3 wherein the target nucleotide sequence is a constant region and the selected nucleotide sequence is a variable region of chromosomal DNA.

7. The reagent complex of claim 2 wherein the target nucleotide sequence and selected nucleotide sequence are messenger RNA sequences.

8. A diagnostic kit comprising the reagent complex of claim 1 and a polynucleotide reagent containing the selected nucleotide sequence.

9. The diagnostic kit of claim 8 wherein the probe polynucleotide is immobilized in the reagent complex.

10. The diagnostic kit of claim 8 wherein the probe polynucleotide contains a moiety immobilized by an affinity reagent and the kit further comprises an immobilized affinity reagent for the moiety.

11. The diagnostic kit of claim 8 wherein the target nucleotide sequence and selected nucleotide sequence are present on a common polynucleotide strand in samples from normal individuals, but are present on separate polynucleotide strands in the event of a translocation.

12. The reagent complex of claim 1 wherein the probe polynucleotide has a third target nucleotide sequence and the labeled polynucleotide is further bound by complementary base pair binding to at least a portion of the third target nucleotide sequence.

13. A method for the determination of a predetermined target nucleotide sequence in the nucleic acid of a biological sample comprising the steps:
(I) contacting the sample with a reagent complex comprising:
(a) a probe polynucleotide having:
(i) a first target binding region which is capable of complementary base pair binding via hydrogen bonds of purine/pyrimidine base pairs to the target nucleotide sequence; and
(ii) a second target binding region which is capable of complementary base pair binding via hydrogen bonds of purine/pyrimidine base pairs to a selected nucleotide sequence; and
(b) a labeled polynucleotide which is bound by complementary base pair binding via hydrogen bonds of purine/pyrimidine base pairs to the probe polynucleotide in at least a portion of the first target binding region and in at least a portion of the second target binding region,
under conditions in which the target nucleotide sequence, if present, displaces the labeled polynucleotide from the first target binding region;
(II) washing the reagent complex;
(III) further contacting the washed reagent complex with a polynucleotide reagent comprising the selected nucleotide sequence under conditions in which the selected nucleotide sequence displaces the labeled polynucleotide from the second target binding region; and
(IV) detecting labeled polynucleotide displaced from the first and second target binding regions.

14. The method of claim 13 wherein the probe polynucleotide is immobilized in the reagent complex.

15. The method of claim 13 wherein the reagent complex is in solution during the contacting step (I) and the probe polynucleotide contains a moiety immobilizable by an affinity reagent.

16. The method of claim 15 wherein the washing step (II) comprises first immobilizing the reagent complex with an immobilized affinity reagent for the moiety and then washing.

17. A method for determining the presence of a target nucleotide sequence and a selected nucleotide sequence within a common polynucleotide strand of the nucleic acid of a biological sample, which comprises the steps:
(I) contacting the sample with a reagent complex comprising:
(a) a probe polynucleotide having:
(i) a first target binding region which is capable of complementary base pairing binding via hydrogen bonds of purine/pyrimidine base pairs to the target nucleotide sequence; and
(ii) a second target binding region which is capable of complementary base pair binding via hydrogen bonds of purine/pyrimidine base pairs to a selected nucleotide sequence; and
(b) a labeled polynucleotlde which is bound by complementary base pair binding via hydrogen bonds of purine/pyrimidine base pairs to the probe polynucleotide in at least a portion of the first target binding region and in at least a portion of the second target nucleotide sequence;
under conditions, including sufficient molar excess of reagent complex relative to anticipated levels of the target nucleotide sequence and of the selected nucleotide sequence, under which sample nucleic acid strands having the target nucleotide sequence and the selected nucleotide sequence, if present within a common sample polynucleotide strand, will displace substantially more labeled polynucleotide strands from the first and second target binding regions of a common probe strand than will target nucleotide sequence and selected nucleotide sequence on separate sample polynucleotide strands; and
(II) detecting labeled polynucleotide displaced from the first and second target binding regions of a common probe strand.

18. The method of claim 17 wherein the molar ratio of reagent complex to either the anticipated level of target nucleotide sequence or selected nucleotide sequence, whichever is higher, is at least about 100:1.

19. The method of claim 17 wherein the ratio is between about $10^3:1$ and about $10^6:1$.

20. The method of claim 16 wherein the target nucleotide sequence and selected nucleotide sequence are chromosomal DNA sequences whose relative position changes with disease states.

21. The method of claim 16 wherein the target nucleotide sequence and selected nucleotide sequence are messenger RNA sequences.

* * * * *